United States Patent [19]

Holaday et al.

[11] Patent Number: 5,114,963
[45] Date of Patent: May 19, 1992

[54] METHOD OF REDUCING SERUM LEVELS OF LIPOPROTEIN(A)

[75] Inventors: John W. Holaday, Rowayton, Conn.; Jonah Shacknai, New York, N.Y.; Leonard L. Mazur, Mountain Lakes, N.J.

[73] Assignee: Medicis Corporation, New York, N.Y.

[21] Appl. No.: 668,304

[22] Filed: Mar. 13, 1991

[51] Int. Cl.⁵ .............................................. A61K 31/38
[52] U.S. Cl. .................................. 514/448; 514/444; 514/824
[58] Field of Search ..................... 514/448, 444, 824

[56] References Cited

U.S. PATENT DOCUMENTS 4,259,508  3/1981  Blum ..................................... 549/72
4,472,424  9/1984  Cavazza .............................. 514/448

OTHER PUBLICATIONS

Gavish, et al., "Lipoprotein(a) reduction by N-acetyl-cysteine", *The Lancet*, vol. 337; pp. 203-204; Jan. 26, 1991.

Description of FLUIMUCIL ™ granules an N-acetyl-cysteine composition produced by Laboratory AR-SAC, Antibes, France, Vidal, 1987.

J. B. Rasmussen, et al., "Reduction in days of illness after long-term treatment with N-acetylcysteine controlled-release tablets in patients with chronic bronchitis", *Eur. Respir J.*, 1.351-355 (1988).

"Academic American Encyclopedia", Prodigy (R) Feb., 1991.

"Principles of Physiology", Ed. R. M. Berne and M. N. Levy pp. 383-385 (1990).

Palma, et al., "N-Acetylcysteine in the Prevention of Cyclophosphamide Induced Haemorrhagic Cystitis", *Int. Surg*, 71:36-37 (1986).

Ziment, I., "Acetylcysteine: A Drug with an Interesting past and a Fascinating Future", *Respir.* 50, suppl. 1, pp. 26-30 (1986).

Turner, et al., "The influence of native porcine gastric mucus gel on hydrogen ion diffusion: the effect of potentially ulcerogenic agents", *J. Pharm, Pharmacol.*, 37:776-780 (1985).

*Primary Examiner*—Jerome D. Goldberg
*Assistant Examiner*—Kimberly R. Jordan
*Attorney, Agent, or Firm*—Jones, Askew & Lunsford

[57] ABSTRACT

The present invention is a method for lowering serum levels of Lp(a), thereby reducing the risk of atherosclerotic disease. Specifically, the present invention comprises administering an effective amount of a N,S-diacyl-L-cysteine to a human or animal with elevated serum levels of Lp(a). The N,S-diacyl-L-cysteines comprise a compound selected from the group having the formula:

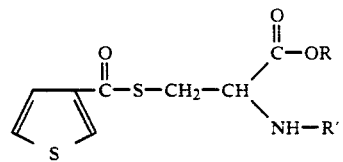

and

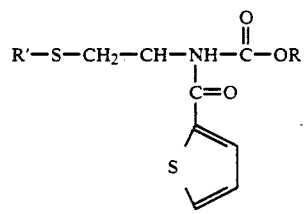

wherein R is selected from the group consisting of hydrogen and an alkyl group containing 1 to 8 carbon atoms and R' is selected from the group consisting of acetyl, benzoly, thenoyl, 2-chromone-carbonyl and succinyl, and pharmaceutically acceptable salts thereof.

14 Claims, No Drawings

METHOD OF REDUCING SERUM LEVELS OF LIPOPROTEIN(A)

TECHNICAL BACKGROUND

The present invention relates to a method of reducing serum levels of lipoprotein(a). More particularly, the present invention is directed to a method of reducing atherosclerotic disease by reducing serum levels of lipoprotein(a) by the administration of an effective amount of an N,S-diacyl-L-cysteine to a human or an animal.

BACKGROUND OF THE INVENTION

Atherosclerosis is the most common form of arteriosclerosis. It is a disease of large and medium-sized arteries, including the coronary arteries that supply blood to the heart. Atherosclerosis is characterized by the buildup of fatty deposits, called plaques, on the inner walls of affected arteries. These plaques consist of materials such as cholesterol, lipids and cellular debris. Plaque buildup can result in loss of arterial elasticity and physical obstruction to blood flow resulting in ischemia. This decrease in blood flow can compromise the functioning of a vital organ, such as the heart or brain.

Atherosclerosis is a common cause of heart diseases including, among others, angina and heart attack. It is also a major cause of stroke. Further, artherosclerosis of vessels serving the extremities can cause loss of circulation to the affected limb. Approximately half the mortality in western society results from heart disease and other blood-vessel diseases resulting from atherosclerosis.

The incidence of atherosclerosis increases with age. Men show clinical manifestations an average of ten years earlier than women, and overt manifestations prior to age forty occur almost entirely in men. Overt manifestations take time to occur because more than a seventy-five percent narrowing of arteries is required to impede blood flow seriously.

The causes of atherosclerosis are not understood completely. However, certain characteristics, called risk factors, often are observed in persons prone to this disorder. These risk factors include, among others, high blood pressure, high serum levels of cholesterol, and high serum levels of low-density lipoproteins (LDLs). Lipoproteins transport lipids in the blood. LDLs are particularly rich in cholesterol and are reported to increase accumulation of cholesterol in body tissues. Genetic factors may play a role in heart disease as individuals with lower than normal percentages of LDL receptors tend to develop atherosclerosis more frequently than do individuals with normal or high percentages of LDL receptors.

Lipoprotein(a), [Lp(a)], is a complex of cholesterol-rich LDLs linked by one or more disulfide bridges to the large glycoprotein known as apo(a). The presence of these Lp(a) complexes at high concentration in the blood greatly increases the risk of atherosclerotic disease.[1,2,3] Lp(a) levels are highly heritable and largely determined by the apo(a) gene locus on chromosome 6q.

[1] Rhoads, G. G., "Lp(a) lipoprotein as a risk factor for myocardial infarction," JAMA, Vol. 256, pps. 2540-2044 (1986).
[2] Durrington, P. N., et al., "Apolipoprotein(a), Ai and B and parental history in men with early onset ischaemic heart disease," LANCET, Vol. 335 (1988).
[3] Hajjar, K. A., et al., "Lipoprotein(a) modulation of endothelial cell surface fibrinolysis and its potential role in atherosclerosis,"NATURE, Vol. 339 (1988).

Currently used hypolipidemic regimens, designed to lower serum lipid levels, do not lower serum Lp(a) satisfactorily. Hypolipidemic regimens such as low-fat diets or diets enriched in monounsaturated fatty acids or ω-6 polyunsaturated fatty acids have little or no effect on serum levels of Lp(a) and fish-oil-based diets cause only a modest reduction in Lp(a). Most drugs have been found to be ineffective or only modestly effective in lowering serum Lp(a).

N-acetylcysteine (NAC) is a mild reducing agent which possesses a free sulfhydryl group that can rupture disulfide bridges. NAC is used most often as a mucolytic in the treatment of chronic bronchitis. Recently, however, NAC was shown to reduce dramatically serum levels of Lp(a).[4] Specifically, oral administration of NAC at 2 grams/day for four weeks followed by 4 grams/day for four weeks, caused serum Lp(a) to decrease by approximately 70%. Other uses of NAC include expectorant, bronchorrheic and mucoregulatory actions, management of acetaminophen poisoning, the scavenging of free radicals liberated by cancer chemotherapy drugs, therapy of connective tissue diseases, solubilization of pigment gallstones, and as a component in life extension diets.

[4] Gavish, et al., "Lipoprotein(a) reduction by N-acetylcysteine," LANCET, Vol. 337, pps. 203-204 (1991).

When ingested in large doses, NAC acts to irritate the gastric mucosa. Natural protection is provided to the mucosal surface of the stomach by a bicarbonate-containing mucus layer known as the gastric mucosal barrier. Buffering by the bicarbonate-containing mucus layer and restraint of convective mixing by the high viscosity of the mucus allow the pH at the cell surface to remain near 7, whereas the pH in the gastric juice in the lumen is 1 to 2. The mucolytic activity of NAC damages the gastric mucosal barrier enabling acid and pepsin to reach the epithelial cell surface and to damage it and the underlying mucosal and submucosal layers of the stomach. This can result in, among others, gastritis, gastric ulcers, diarrhea and their concomitant discomforts and dangers. Experiments show that NAC significantly increases the rate of and reduces the time for hydrogen ions to traverse a mucus layer.

What is needed is a compound which has the therapeutic effects of NAC, including lowering serum levels of Lp(a), but which does not adversely effect the gastric mucosa.

SUMMARY OF THE INVENTION

The present invention is a method for lowering serum levels of Lp(a), thereby reducing the risk of atherosclerotic disease. Specifically, the present invention comprises administering an effective amount of a N,S-diacyl-L-cysteine to a human or animal with elevated serum levels of Lp(a). The N,S-diacyl-L-cysteines comprise a compound selected from the group having the formula:

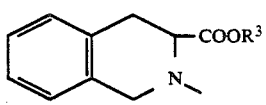

A

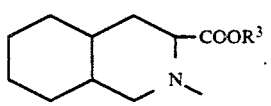

B

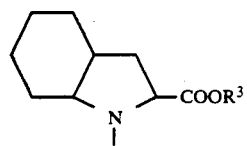
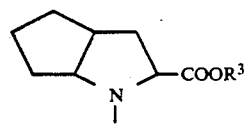
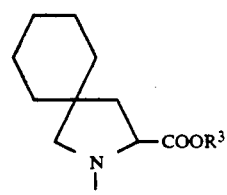
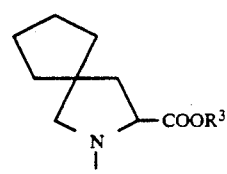
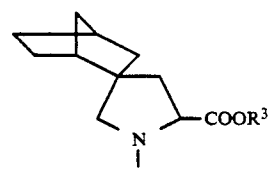
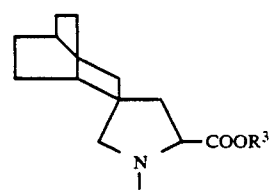
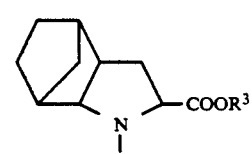
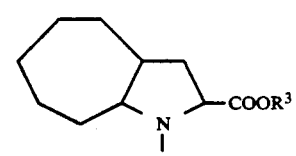
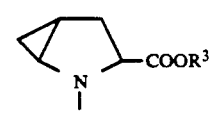

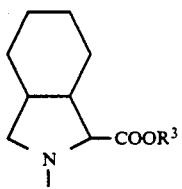
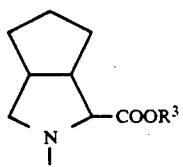
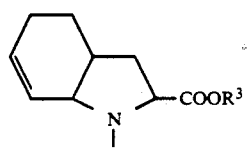
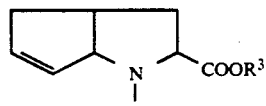
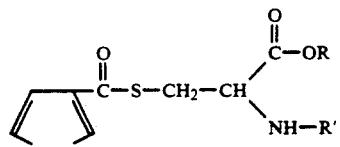

and

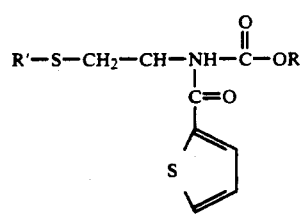

wherein R is selected from the group consisting of hydrogen and an alkyl group containing 1 to 8 carbon atoms and R' is selected from the group consisting of acetyl, benzoyl, thenoyl, 2-chromone-carbonyl and succinyl, and pharmaceutically acceptable salts thereof.

The N,S-diacyl-L-cysteines can be administered orally, by aerosol, suppository, transdermal device or by injection in a pharmaceutically acceptable carrier. To be effective, the N,S-diacyl-L-cysteines should be administered over a prolonged period of time.

Accordingly, it is an object of the present invention to provide a method for reducing serum levels of LDLs; specifically, of Lp(a).

It is another object of the present invention to provide a method for reducing the risk of atherosclerotic diseases.

It is another object of the present invention to provide a method for reducing the risk of thrombotic diseases.

It is another object of the present invention to provide a method for reducing serum levels of Lp(a) comprising the oral administration of a N,S-diacyl-L-cysteine.

It is another object of the present invention to provide a method for reducing serum levels of Lp(a) comprising injecting into the bloodstream an effective dose of a N,S-diacyl-L-cysteine.

It is another object of the present invention to provide a method for reducing serum levels of Lp(a) which does not cause gastric distress.

It is another object of the present invention to provide a method for reducing serum levels of Lp(a) which is convenient and easy for the patient with minimal gastrointestinal irritation.

These and other objects, features and advantages of the present invention will become apparent after a review of the following detailed description of the disclosed embodiments and the appended claims.

DETAILED DESCRIPTION

The present invention comprises a method of reducing serum levels of lipoprotein(a), Lp(a), in a human or animal. More particularly the present invention includes a method of reducing atherosclerotic and thrombotic diseases in humans and animals comprising the administration of an effective amount of a N,S-diacyl-L-cysteine to the human or animal. N,S-diacyl-L-cysteines, at dosages effective in reducing serum levels of Lp(a), can be administered over prolonged periods of time with minimal toxic side-effects. Maintenance therapy with these compounds can significantly reduce serum levels of Lp(a).

The compounds which can be used in practicing the present invention are selected from the group having the following formula:

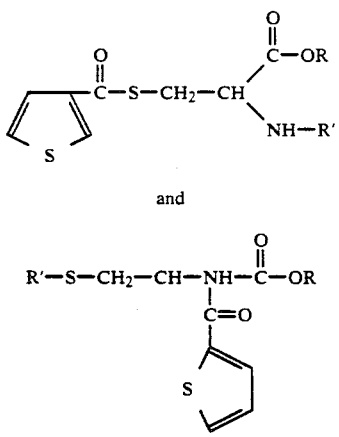

and wherein R is selected from the group consisting of hydrogen and an alkyl group containing 1 to 8 carbon atoms and R' is selected from the group consisting of acetyl, benzoyl, thenoyl, 2 chromone-carbonyl and succinyl, and pharmaceutically acceptable salts thereof. The preferred N,S-diacyl-L-cysteine is N-acetyl, S-2-thenoyl cysteine and its salts or esters. Synthesis of the N,S-diacyl-L-cysteine compounds is described in U.S. Pat. No. 4,259,508, which is incorporated herein by reference.

The preferred mode of administration of N,S-diacyl-L-cysteines in the present invention is oral. They can be dissolved in any pleasant-tasting food such as juice, soda or other liquid or can be admixed with solid food. N,S-diacyl-L-cysteines can also can be administered orally by encapsulating a specified amount of the compound in a capsule to be taken by the patient at prescribed intervals. The compound can be encapsulated with or without an inert carrier. The compound also can be formulated in time-release form. A major advantage of the present invention is that oral administration of the N,S-diacyl-L-cysteine results in minimal irritation of the gastric mucosa.

Although the preferred mode of administration of N,S-diacyl-L-cysteines is oral, it is to be understood that N,S-diacyl-L-cysteines can be administered by injection. Injection can be intravenous, intramuscular, intraperitoneal or subcutaneous. Carrier solutions which may be employed in practicing the present invention include, but are not limited to, saline (8.5 to 9.5 grams of NaCl/1000 ml sterile water), Ringer's solution, lactated Ringer's solution, Krebs-Ringer's solution, and various sugar solutions. All of these solutions are well known to those of ordinary skill in the art. Other isotonic solutions can be used to prepare a solution of the N,S-diacyl-L-cysteine. However, it is to be understood that the present invention may be administered as a solution that is not isotonic. N,S-diacyl-L-cysteine also can be administered by mucosal absorption. For example, by nasal aerosol, rectal suppository, or buccal pellet. It can also be administered by transdermal patch.

The optimal dose of the N,S-diacyl-L-cysteine is between approximately 100 to 3000 mg per day for children and between approximately 200 and 10,000 mg per day for adults. The dose can be higher if needed. The preferred dose of N,S-diacyl-L-cysteine is between approximately 200 and 2000 mg per day for children and between approximately 200 and 5000 mg per day for adults. Preferably, the compound can be administered from approximately 1 to 4 times per day. It is to be understood that the number of doses per day can be varied depending upon the amount of compound per dose.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE I

The present invention includes the administration of an N-acetyl-S-thenoyl-cysteine in oral form. In one embodiment according to the present invention, 2000 mg of N-acetyl-S-thenoyl-cysteine are dissolved in six ounces of a flavored and sweetened syrup. For use by adults, one ounce is taken every four hours for a total of six doses per 24 hour period. This dosage schedule is maintained for as long as required.

EXAMPLE II

In another embodiment, 2000 mg of N-acetyl-S-thenoyl-cysteine are compounded into four tablets each containing 500 mg of N-acetyl-S-thenoyl-cysteine. For use by adults, one capsules is taken every six hours for a total of four doses per 24 hour period. This dosage schedule is maintained for as long as required.

EXAMPLE III

In another embodiment, 600 mg of N-acetyl-S-thenoyl-cysteine are dissolved in six ounces of a flavored and sweetened syrup. For use by children, one ounce is taken every four hours for a total of six doses per 24 hour period. This dosage schedule is maintained for as long as required.

EXAMPLE IV

A patient with a Lp(a) serum level of 60 mg/dl is given four 500 mg tablets of N-acetyl-S-thenoyl-cysteine daily (2000 mg/day) for eight weeks. Serum levels of Lp(a) fall to 30 mg/dl within six days and remain at or below this level as long as therapy is continued. Following discontinuation of N-acetyl-S-thenoyl-cysteine, serum Lp(a) returns to pretreatment levels within five days.

EXAMPLE V

A patient with a Lp(a) serum level of 65 mg/dl is treated with an oral dose of N-acetyl-S-thenoyl-cysteine of 3000 mg per day for twenty weeks. Serum levels of Lp(a) fall to 24 mg/dl and remain at or below this level as long as therapy is continued. Following discontinuation of N-acetyl-S-thenoyl-cysteine, serum Lp(a) returns to pretreatment levels.

EXAMPLE VI

Four patients with Lp(a) serum levels between 50 and 80 mg/dl are are divided into two groups. Group 1 receives tablets containing 500 mg of N-acetyl-S-thenoyl-cysteine four times per day (2000 mg/day) for 70 days. Group 2 receives tablets containing 500 mg of starch four times per day (2000 mg/day) for 70 days. No dietary restriction are imposed during the study period. Fasting blood samples are drawn from each patient twice each week during the treatment period, at the end of the treatment period, and weekly for six weeks after the end of the treatment period. Serum Lp(a) levels fall in the Group 1 patients during the treatment period, but increase to initial levels after discontinuation of N-acetyl-S-thenoyl-cysteine. Serum Lp(a) levels remain high in Group 2 patients during the treatment period and after discontinuation of the treatment.

It should be understood, of course, that the foregoing relates only to preferred embodiments of the present invention and that numerous modifications or alterations may be made therein without departing from the spirit and the scope of the invention as set forth in the appended claims.

We claim:

1. A method for reducing the serum level of lipoprotein(a) in a human or animal with an elevated level of lipoprotein(a) comprising administering to the human or animal an amount of a compound selected from the group consisting of compounds with the following formula:

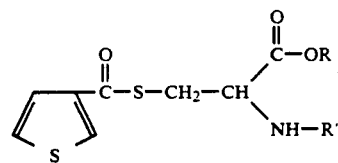

and

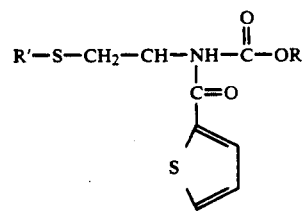

wherein R is selected from the group consisting of hydrogen and an alkyl group containing 1 to 8 carbon atoms and R' is selected from the group consisting of acetyl, benzoyl, thenoyl, 2 chromone-carbonyl and succinyl, and pharmaceutically acceptable salts thereof sufficient to reduce the serum level of lipoprotein(a).

2. The method of claim 1, wherein R' is thenoyl.

3. The method of claim 1, wherein R is a hydrogen.

4. The method of claim 1, wherein the compound is N-acetyl-S-2-thenoyl cysteine and its salts.

5. A method for reducing the serum level of lipoprotein(a) in a human or animal with an elevated level of lipoprotein(a) comprising the step of orally administering to the human or animal an amount of a compound selected from the group consisting of compounds with the following formula:

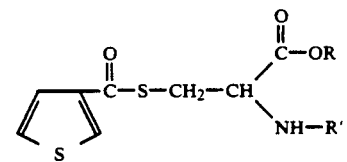

and

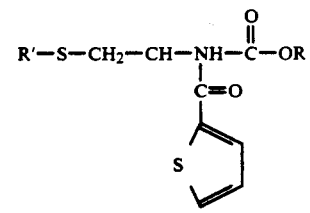

wherein R is selected from the group consisting of hydrogen and an alkyl group containing 1 to 8 carbon atoms and R' is selected from the group consisting of acetyl, benzoyl, thenoyl, 2 chromone-carbonyl and succinyl, and pharmaceutically acceptable salts thereof sufficient to reduce the serum level of lipoprotein(a).

6. The method of claim 5, wherein R' is thenoyl.

7. The method of claim 5, wherein R is a hydrogen.

8. The method of claim 5, wherein the compound is N-acetyl-S-2-thenoyl cysteine and its salts.

9. The method of claim 5, wherein the compound is administered in a form selected from the group consisting of tablets, capsules, and powders.

10. The method of claim 5, wherein the compound is administered as a solution.

11. A method for reducing the serum level of lipoprotein(a) in a human or animal with an elevated level of lipoprotein(a) comprising the step of injecting into the human or animal a solution with an amount of a compound selected from the group consisting of compounds with the following formula:

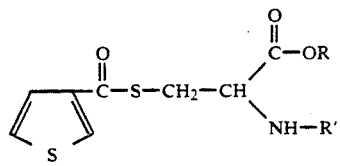

and

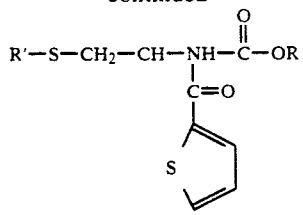

wherein R is selected from the group consisting of hydrogen and an alkyl group containing 1 to 8 carbon atoms and R' is selected from the group consisting of acetyl, benzoyl, thenoyl, 2 chromone-carbonyl and succinyl, and pharmaceutically acceptable salts thereof sufficient to reduce the serum level of lipoprotein(a).

12. The method of claim 11, wherein R' is thenoyl.
13. The method of claim 11, wherein R is a hydrogen.
14. The method of claim 11, wherein the compound is N-acetyl-S-2-thenoyl cysteine and its salts.

* * * * *